United States Patent

Hara et al.

[11] Patent Number: 5,969,194
[45] Date of Patent: Oct. 19, 1999

[54] PROCESS FOR PREPARING 1, 6-HEXANEDIOL

[75] Inventors: Yoshinori Hara; Koetsu Endou, both of Kanagawa; Seijiro Nishimura, Mie, all of Japan

[73] Assignee: Mitsubishi Chemical Corporation, Tokyo, Japan

[21] Appl. No.: 09/034,334

[22] Filed: Mar. 4, 1998

[30] Foreign Application Priority Data

| Mar. 4, 1997 | [JP] | Japan | 9-048889 |
| Jul. 30, 1997 | [JP] | Japan | 9-204252 |
| Aug. 13, 1997 | [JP] | Japan | 9-218537 |
| Aug. 13, 1997 | [JP] | Japan | 9-218538 |
| Sep. 2, 1997 | [JP] | Japan | 9-236943 |

[51] Int. Cl.$^6$ ............... C07C 27/10; C07C 31/18
[52] U.S. Cl. ............... 568/700; 568/852; 560/1
[58] Field of Search ............... 568/700, 852; 560/1

[56] References Cited

U.S. PATENT DOCUMENTS

| 3,524,892 | 8/1970 | Horlenko et al. | 568/700 |
| 3,933,930 | 1/1976 | Dougherty et al. | 568/700 |
| 4,346,240 | 8/1982 | Grey et al. | 568/700 |
| 4,359,404 | 11/1982 | Grey et al. | 568/700 |

*Primary Examiner*—Louise N. Leary
*Attorney, Agent, or Firm*—Oblon, Spivak, McClelland, Maier & Neustadt, P.C.

[57] ABSTRACT

A process for preparing 1,6-hexanediol comprising hydrogenating a starting material containing at least one compound selected from the group consisting of adipic acid, ε-hydroxycaproic acid, ε-caprolactone and oligomers of ε-caprolactone, preferably a substance recovered from a reaction mixture resulting from liquid phase oxidization of cyclohexane for the production of cyclohexanol and cyclohexanone, in a liquid phase in the presence of a solid catalyst containing ruthenium and tin.

14 Claims, No Drawings

PROCESS FOR PREPARING 1,6-HEXANEDIOL

FIELD OF THE INVENTION

This invention relates to a process for preparing 1,6-hexanediol. More particularly, it relates to a process for preparing 1,6-hexanediol by directly hydrogenating a starting compound selected from adipic acid, ε-hydroxycaproic acid, ε-caprolactone and oligomers of ε-caprolactone without involving esterification.

BACKGROUND OF THE INVENTION 1,6-Hexanediol is useful as a starting material for producing polyurethane, polyester-type plasticizers, unsaturated polyesters, 1,6-hexanediol diacrylate, etc. (see JP-A-62-184640, JP-A-56-78844, JP-A-3-227389, and JP-A-5-59306, the term "JP-A" as used herein means an "unexamined published Japanese patent application").

It is known that 1,6-hexanediol is prepared by a process comprising oxidizing cyclohexane to form adipic acid, ε-hydroxycaproic acid, etc., esterifying these carboxylic acids with methanol, etc., and reacting the resulting esters with hydrogen in the presence of a catalyst for hydrogenation (see JP-B-53-33567 (the term "JP-B" as used herein means an "examined published Japanese patent application") and JP-A-51-108040). This process is disadvantageous in that an esterification step is required and that the hydrogenation should be conducted in the presence of a copper catalyst under high temperature and high pressure conditions.

There have been proposed several processes in which 1,6-hexanediol is obtained through direct hydrogenation of the starting compound without involving esterification. For example, JP-A-47-4767 and JP-A-49-132003 disclose hydrogenation in the presence of a cobalt catalyst. JP-B-49-33171 and JP-A-9-5918.8 propose using a rhenium catalyst and a Raney nickel catalyst, respectively. However, these processes have their several problems such that the reaction conditions are severe or the catalyst activity is unsatisfactory.

Further, JP-A-47-4764 and JP-A-48-14609 teach a process comprising catalytically hydrogenating a starting carboxylic acid in the form of an alkali metal salt in a buffer solution. This process is disadvantageous in that an alkali equivalent to the carboxyl group of the starting compound is required and that the hydrogenation should be catalytically carried out in a buffer solution by using a cobalt catalyst under high pressure.

SUMMARY OF THE INVENTION

An object of the present invention is to provide a process for preparing 1,6-hexanediol comprising directly hydrogenating at least one starting compound selected from adipic acid, ε-hydroxycaproic acid, ε-caprolactone and oligomers of ε-caprolactone under a relatively mild condition.

Another object of the present invention is to provide a process for preparing 1,6-hexanediol in which the catalyst used exhibits high activity and high selectivity and maintains these properties stably even in a long-time reaction.

The above objects are accomplished by a process for preparing 1,6-hexanediol comprising hydrogenating a starting material containing at least one starting compound selected from the group consisting of adipic acid, ε-hydroxycaproic acid, ε-caprolactone and oligomers of ε-caprolactone in a liquid phase in the presence of a solid catalyst containing ruthenium and tin.

According to the present invention, 1,6-hexanediol can be prepared in high yield and at high selectivity.

DETAILED DESCRIPTION OF THE INVENTION

The starting compounds which can be used in the present invention are adipic acid, ε-hydroxycaproic acid, ε-caprolactone and oligomers of ε-caprolactone. These compounds can be used either individually or as a mixture thereof. While the starting compound used in the present invention could be subjected to hydrogenation after once being converted to its ester with methanol, etc., the process of the present invention is characterized in that the starting compound is directly subjected to hydrogenation.

Of the starting compounds the preferred are adipic acid and/or ε-hydroxycaproic acid, etc. which are by-produced in oxidation of cyclohexane with oxygen for the production of cyclohexanol and cyclohexanone. For instance, JP-B-6-99345 discloses a process for producing cyclohexanol and cyclohexanone comprising oxidizing cyclohexane with oxygen in the presence of an oxidation catalyst, such as a cobalt catalyst, at about 100 to 200° C. under a pressure of about 2 to 20 kg/cm²G, and that the by-produced adipic acid, etc. can be recovered from the reaction mixture for use in the production of 1,6-hexanediol. The by-produced adipic acid, etc. are recovered by saponifying the reaction mixture by addition of an aqueous alkali solution, such as an aqueous sodium hydroxide solution, allowing the saponified mixture to stand to separate into an aqueous phase and an oily phase. The aqueous phase contains alkali salts of the by-produced adipic acid, ε-hydroxycaproic acid, and other by-produced carboxylic acids. The aqueous phase is neutralized with sulfuric acid, etc. and the carboxylic acids in the aqueous phase are extracted with an organic solvent to form an organic solvent solution. The organic solvent is removed from the solution by evaporation to give a carboxylic acid mixture containing the desired starting compounds. Suitable extractants include ketones, such as methyl isobutyl ketone, methyl ethyl ketone, and cyclohexanone, esters, such as ethyl acetate, butyl acetate, and methyl caproate, and alcohols, such as cyclohexanol.

The concentration of the desired starting compounds in the resulting carboxylic acid mixture is usually 20 to 40% by weight. In expressing the "concentration of the starting compounds" as referred to in the present invention, the concentrations of ε-caprolactone and oligomers of ε-caprolactone are calculated as converted to ε-hydroxycaproic acid.

While the carboxylic acid mixture as recovered can be subjected to hydrogenation as such, it is desirable for the mixture to be concentrated to increase the concentration of the starting compounds to 45 to 80% by weight, particularly 60 to 80% by weight. Use of the thus concentrated mixture will make the apparatuses for hydrogenation and for subsequent isolation and purification smaller-sized and save hydrogen for hydrogenation. Concentration of the carboxylic acid mixture to a desired starting compound concentration is carried out by distilling the mixture under reduced pressure to drive off low-boiling components. Additionally, the concentrated carboxylic acid mixture may be dissolved in an aqueous alkali solution, such as a sodium hydroxide aqueous solution, to form an aqueous solution of carboxylic acid salts, which is then neutralized with sulfuric acid, etc. to precipitate a solid comprising the starting compounds in a further increased concentration. Since the resulting aqueous mother liquor also contains the starting compounds dissolved therein, the filtrate after collecting the solid can be mixed with an organic solvent such as methyl isobutyl ketone to extract the starting compounds, and the extract is subjected to hydrogenation in combination with the solid. Where the above procedure is followed, not only is concentration of the starting compounds achieved but the components that would become catalyst poison in the hydrogenation reaction can be left in the aqueous phase, thereby making it possible to perform the hydrogenation reaction in a stable manner for an extended period of time. It is preferred for the aqueous solution after neutralization to contain sodium sulfate in a high concentration, e.g., 15 to 25% by weight. Therefore it is preferred to previously add sodium sulfate to the carboxylic acid aqueous solution before neutralization so that the aqueous solution after neutralization may have the preferred sodium sulfate concentration.

The catalyst which can be used in the present invention contains ruthenium and tin as active components. A catalyst additionally containing platinum has further improved catalytic activity. The catalyst may be made from these active components with no carrier (non-supported type) but are preferably made from these active components and a porous carrier.

The non-supported type catalyst containing the active components can be prepared by a method using a reducing agent or a coprecipitation method as disclosed in *Journal of Catalyst*, Vol. 121, No. 1, p. 165 (1990).

The porous carrier to be used in the supported type catalyst is conventional, including activated carbon, diatomaceous earth, alumina, silica, titania, and zirconia. If desired, two or more porous carriers may be used in combination. Activated carbon is a preferred porous carrier. It is desirable for the porous carrier, especially activated carbon, to be pretreated with an acid. Such pretreatment generally results in improved catalytic activity and selectivity. The acid treatment is carried out by immersing the porous carrier into an aqueous solution of a mineral acid, e.g., nitric acid, hydrochloric acid, sulfuric acid, perchloric acid, hypochloric acid, etc., and maintaining it at room to elevated temperature for several minutes to several hours. In general, the desired effect of the acid treatment is attained in a shorter time at a higher temperature of the acid solution. The acid treatment is usually conducted by using an aqueous nitric acid solution kept at 30 to 100° C., preferably 50 to 90° C. The aqueous nitric acid solution preferably has a concentration of 1 to 75% by weight, particularly 5 to 60% by weight. In the acid treatment, the time required depends on the temperature. For example, at around 90° C. it needs at least 1 minute, usually 10 minutes or longer. There is no particular upper limit to the time. Usually an acid treatment of about 1 hour would be enough but can be prolonged if desired. While the reason the acid-treated porous carrier provides a catalyst of higher performance is unclear, it appears that the acid treatment can remove impurities in the porous carrier that might adversely affect the catalytic performance or impart some oxygen-containing functional groups to the porous carrier.

The acid-treated porous carrier is thoroughly washed with water to remove any acid remained thereon. The washed porous carrier is preferably dried to reduce the water content to 7% by weight or less to ensure further improvement in catalytic performance. The water content of the carrier is preferably as low as possible, usually 5% by weight or lower, particularly 1% by weight or lower. It can be dried in any conventional manner. For example, drying is effected by heating at 100° C. or higher in a dry gas stream, e.g., air or nitrogen, or heating at 50° C. or higher under reduced pressure of 10 mmHg or lower. The term "water content" as used herein is intended to mean a weight loss on heating from room temperature up to 185° C. in TG-DTA (i.e., Thermogravity-Differential Thermal Analysis). It is not clear why the reduction of water content of the porous carrier to 7% by weight or less favors the catalytic performance, but it is believed that the surface of the porous carrier undergoes some changes on drying thereby inducing changes of the active components supported thereon in form or distribution.

The manner of supporting the active components on the porous carrier is not limited, and any conventional technique employed in the preparation of supported type catalysts, such as an impregnation method, an ion exchange method, a sol-gel method, can be used. An impregnation method is preferred for its convenience. In the impregnation method, compounds of the active components, i.e., a ruthenium compound, a tin compound and, if desired, a platinum compound, are dissolved in water or any appropriate solvent, and the porous carrier is immersed therein to adsorb the compounds. The amounts of the ruthenium compound and the tin compound supported on the carrier are each 0.5 to 50% by weight, preferably 1 to 20% by weight, in terms of metallic ruthenium or tin, based on the carrier. For achieving substantial improvement in catalytic activity, the amount of the platinum compound to be supported on the carrier is preferably 0.1 to 5 times by weight, based on the ruthenium both in terms of metals.

The compounds of ruthenium, tin or platinum which are usually used in the preparation of the catalyst include mineral acid salts of the metal, such as a nitrate, a sulfate and a hydrochloride. Organic acid salts such as an acetate, hydroxides, oxides, organometallic compounds, and complex salts of the metal are also useful.

The order of addition of the active components to the carrier is not limited. The active components can be adsorbed simultaneously by using a solution containing all of them or successively by using a plurality of solutions containing one or some of them. It is also possible to add an active component in several times. In a preferred manner, a ruthenium compound and a tin compound are first supported on the carrier and, after drying, converted to the respective metals by reduction, and then platinum compound is supported on the carrier.

After the carrier is brought into contact with a solution(s) containing the active component(s) to adsorb the active components, the carrier is dried. Where the active components are adsorbed in a plurality of times, the carrier is preferably dried for each treatment. The drying temperature is preferably 200° C. or lower, at which the carrier having adsorbed thereon the active components is held under reduced pressure or in a stream of air or a dry inert gas, such as nitrogen. The product as dried is useful as a catalyst but is usually used after reduction. Prior to reduction, the dried carrier may be held in an air or inert gas stream at 100 to 600° C. The reduction can be carried out by either a liquid phase reduction method or a gaseous phase reduction method in a conventional manner, usually in a gaseous phase at 100 to 600° C., preferably 200 to 550° C. Hydrogen, methanol, etc. is used as reducing gas, with hydrogen being preferred. The reducing gas can be used as diluted with an inert gas. The reduction is preferably conducted at a temperature of 260° C. or higher, particularly 300 to 550° C., at a gas hourly space velocity of 10000 $hr^{-1}$ or less, particularly 500 to 7500 $hr^{-1}$. By this reduction there is obtained a catalyst of high activity and high selectivity.

In the present invention, the starting compounds are hydrogenated in a liquid phase using the thus prepared catalyst. The hydrogenation is carried out usually at a temperature of 50 to 350° C., preferably 100 to 250° C., under a pressure of 0.1 to 30 MPa, preferably 1 to 25 MPa, either in a suspended bed-type reactor or a fixed bed-type reactor and either in a continuous process or a batch process. Continuous process using a suspended bed-type reactor is preferred. A continuous process using a multistage-type reactor in which the reactant passes successively through a plurality of reaction zones is preferred.

While not essential, a solvent is preferably used for the hydrogenation reaction. Water is a preferred solvent. In addition, any solvent that has no adverse influence on the reaction can also be used. Useful solvents include alcohols, such as methanol, ethanol, octanol, and dodecanol; ethers, such as tetrahydrofuran, dioxane, tetraethylene glycol, and dimethyl ether; and hydrocarbons, such as hexane, cyclohexane, and decalin.

It is preferred that sodium sulfate be present in the liquid phase where the hydrogenation reaction is conducted. The presence of sodium sulfate is generally effective in improving conversion rate and selectivity. Sodium sulfate is preferably present in a concentration of 1000 ppm by weight or higher. While there is no particular upper limit of the sodium sulfate concentration, because the conversion rate and selectivity will be saturated eventually as the concentration increases, a preferred upper limit is 10% by weight.

It is also preferred that an alkali salt of the starting compound(s) be present in the liquid phase. The presence of the alkali salt is effective in preventing the catalyst from being poisoned thereby stabilizing the hydrogenation reaction for a prolonged period of time. It is particularly effective that the alkali salt of starting compound(s) be present where the by-product obtained in the production of cyclohexanol and cyclohexanone by oxidation of cyclohexane with oxygen is employed as a starting material as described above. The alkali salt of the starting compound can be incorporated into the liquid phase by adding an alkali, such as a sodium hydroxide aqueous solution, to the liquid phase to neutralize part of the starting compound in the phase thereby forming an alkali salt, or by supplying the starting compound a part of which has been converted to its alkali salt. In either case, it is preferred that 0.1 to 80 mol %, more preferably 1 to 50 mol %, particularly 5 to 50 mol %, of the carboxyl groups of the total starting compounds to be hydrogenated have the form of an alkali salt ($\epsilon$-caprolactone and oligomers of $\epsilon$-caprolactone are calculated as $\epsilon$-hydroxycaproic acid). Since the part of the starting compounds that has an alkali salt form is not hydrogenated, it can be recovered from the hydrogenation reaction mixture and reused.

After completion of the hydrogenation, the reaction mixture is distilled to obtain 1,6-hexanediol as a distillate. The unreacted starting compounds and esters thereof, sodium sulfate, carboxylic acid salts of the starting compounds, and the like which remain in the distillation residue can be collected and reused.

The present invention will now be illustrated in greater detail with reference to Examples, but it should be understood that the present invention is not construed as being limited thereto. Unless otherwise noted, all the percents and parts are by weight. The carriers, catalysts and starting materials used in Examples were prepared as follows.

Preparation of Carrier:

Activated carbon (CX-2 produced by Mitsubishi Chemical Corporation; particle size: 10 to 20 mesh, hereinafter the same) was put in a 50% nitric acid aqueous solution and maintained at 95° C. for 3 hours, followed by filtration. The collected activated carbon was thoroughly washed with water and dried at 80° C. under reduced pressure of 2 mmHg for 5 hours to prepare an activated carbon carrier (designated carrier A).

Activated carbon (CX-2) was put in a 50% nitric acid aqueous solution and maintained at 95° C. for 3 hours, followed by filtration. The collected activated carbon was thoroughly washed with water and dried at 80° C. and 2 mmHg for 5 hours to prepare an activated carbon carrier having a water content of 0.95% (designated carrier B).

Activated carbon (CX-2) was washed with water and dried at 80° C. and 2 mmHg for 5 hours to prepare an activated carbon carrier having a water content of 0.95% (designated carrier C).

Activated carbon (CX-2) was put in a 50% nitric acid aqueous solution and maintained at 95° C. for 5 hours, followed by filtration. The collected activated carbon was thoroughly washed with water and dried at room temperature and 2 mmHg for 5 hours to prepare an activated carbon carrier having a water content of 7.79% (designated carrier D).

Preparation of Catalyst:

In a flask was put 3.6 ml of a 5N HCl aqueous solution, and 1.578 g of $RuCl_3.3H_2O$ was added thereto. To the flask were further put $SnCl_2.2H_2O$ and $H_2PtCl_6.6H_2O$ in amounts giving a Ru:Sn:Pt weight ratio shown in Table 1 below and dissolved. To the resulting solution was added 8.55 g of carrier A to absorb the solution. The flask was set in an evaporator, and water was evaporated at 60° C. and 25 mmHg. The carrier was further held at 150° C. for 2 hours in an argon stream. Then the compounds adsorbed on the carrier were reduced with hydrogen in a gaseous phase for 2 hours at the temperature and gas hourly space velocity (GHSV) shown in Table 1 to prepare catalysts A to I.

TABLE 1

| Cata- | Reducing Conditions | | Composition of |
| --- | --- | --- | --- |
| lyst | GHSV (hr$^{-1}$) | Temp. (° C.) | Catalyst (wt %) |
| A | 750 | 450 | 6%Ru-5%Sn-2%Pt/ac* |
| B | 750 | 450 | 6%Ru-5%Sn/ac |
| C | 750 | 450 | 6%Ru-5%Sn-1%Pt/ac |
| D | 750 | 450 | 6%Ru-5%Sn-3.5%Pt/ac |
| E | 750 | 450 | 6%Ru-9%Sn-3.5%Pt/ac |
| F | 8000 | 450 | 6%Ru-5%Sn-2%Pt/ac |
| G | 750 | 350 | 6%Ru-5%Sn-2%Pt/ac |
| H | 750 | 250 | 6%Ru-5%Sn-2%Pt/ac |
| I** | 750 | 450 | 6%Ru-5%Sn-2%Pt/ac |

Note: *"ac" stands for activated carbon (hereinafter the same).
**$Na_2SnO_3$ was used in place of $SnCl_2.2H_2O$.

In a flask was put 3.6 ml of a 5N HCl aqueous solution, and 1.578 g of $RuCl_3.3H_2O$, 0.95 g of $SnCl_2.2H_2O$, and 0.258 g of $H_2PtCl_6.6H_2O$ were dissolved therein. To the resulting solution was added 8.55 g of carrier B, C or D to absorb the solution. The flask was set in an evaporator, and water was evaporated at 60° C. and 25 mmHg. The carrier was further held at 150° C. for 2 hours in an argon stream. Then the compounds adsorbed on the carrier were reduced in a hydrogen stream at 450° C. for 2 hours to prepare catalysts J to L comprising 6% Ru, 5% Sn and 1% Pt on activated carbon. The particulars of catalysts J to L are tabled below.

TABLE 2

| Catalyst | Carrier | Composition of Catalyst (wt %) |
|---|---|---|
| J | B | 6%Ru-5%Sn-1%Pt/ac |
| K | C | 6%Ru-5%Sn-1%Pt/ac |
| L | D | 6%Ru-5%Sn-1%Pt/ac |

In a flask was put 3.6 ml of a 5N HCl aqueous solution, and 1.57 g of $RuCl_3.3H_2O$, 0.814 g of $H_2PtCl_6.6H_2O$, and 0.95 g of $SnCl_2.2H_2O$ were dissolved therein. To the resulting solution was added 8.55 g of silica (special grade 12, produced by Fuji Davison Chemical Co., Ltd.; specific surface area: 679 m$^2$/g; pore volume: 0.37 ml/g) to absorb the solution. The flask was set in an evaporator, and water was evaporated at 60° C. and 25 mmHg. The carrier was further held at 150° C. for 2 hours in an argon stream. Then the compounds adsorbed on the silica carrier were reduced in a hydrogen stream at 450° C. for 2 hours to prepare catalyst M having a composition of 6% Ru-5% Sn-3.5% Pt/SiO$_2$.

Preparation of Starting Material:

Liquid cyclohexane was oxidized by bubbling oxygen to produce cyclohexanol and cyclohexanone. The reaction mixture was extracted with a sodium hydroxide aqueous solution to obtain an aqueous solution containing carboxylic acids. The aqueous solution was neutralized with sulfuric acid and then mixed with methyl isobutyl ketone to extract the carboxylic acid. The extract was evaporated to remove the solvent, and the residue was used as a starting material (designated as starting material A).

The carboxylic acid contents of the resulting starting material were determined by liquid chromatography wherein starting material dissolved in sodium hydroxide aqueous solution was injected in the column and then 0.1% trifluoroacetic acid aqueous solution was introduced as an eluent, and the carboxyl group content of the starting material was obtained by alkali titration wherein starting material dissolved in water was used as a sample (hereinafter the same). These analytic results of starting material A are shown below.

Adipic acid: 21.8%
ε-Hydroxycaproic acid: 16.1%
Carboxyl group content: 8.03 mmol/g Starting material B was prepared by distilling starting material A at a liquid temperature of 100° C. under reduced pressure of 2 to 3 mmHg to remove low-boiling components to obtain the residue having the following composition.

Adipic acid: 43.8%
ε-Hydroxycaproic acid: 23.3%
Carboxyl group content: 9.10 mmol/g Starting material C was prepared by distilling residue obtained in the same manner as for starting material A at a liquid temperature of 100° C. under reduced pressure of 2 to 3 mmHg to remove low-boiling components to obtain the residue having the following composition.

Adipic acid: 42.1%
ε-Hydroxycaproic acid: 24.9%
Glutaric acid: 6.2%
δ-hydroxyvaleric acid: 10.4%
Carboxyl group content: 8.07 mmol/g Starting material D having the following composition was prepared in the same manner as for starting material C.

Adipic acid: 32.8%
ε-Hydroxycaproic acid: 28.7%
Glutaric acid: 6.2%
δ-hydroxyvaleric acid: 11.4%
Carboxyl group content: 9.19 mmol/g Starting material E was prepared as follows. To 100 parts of starting material C was added 250 parts of a 20% sodium hydroxide aqueous solution to form a uniform solution. To the solution was added a 30% sulfuric acid aqueous solution in such an amount that the sulfuric acid was 0.74 times the molar amount of sodium hydroxide. Whereupon the mixture was separated into a lower aqueous phase and an upper oily phase. The solution with two phases was cooled with ice, and the precipitate thus formed was collected by filtration. Starting material E had the following composition.

Adipic acid: 67.5%
ε-Hydroxycaproic acid: 4.1%
Glutaric acid: 0.2%
δ-hydroxyvaleric acid: 0.7%
Carboxyl group content: 10.1 mmol/g Starting material F having the following composition was prepared in the same manner as for starting material C.

Adipic acid: 32.8%
ε-Hydroxycaproic acid: 28.7%
Carboxyl group content: 9.19 mmol/g
Sodium sulfate: 800 ppm (measured by XRF (i.e., X-Ray Fluorescence Analysis))

EXAMPLES 1 TO 15

In a 200 ml autoclave with induction stirring device were charged 8.5 g of adipic acid, 11.5 g of ε-caprolactone, water, and the catalyst shown in Table 3 below in an argon atmosphere. Hydrogen was introduced up to a pressure of 1 MPa, and the autoclave was heated. When a prescribed temperature was reached, hydrogen was introduced to a prescribed pressure, and the reaction was allowed to proceed at that temperature under that pressure for a prescribed period of time. After completion of the reaction, the carboxyl group content in the reaction mixture was analyzed by titration to calculate the conversion rate of the starting compounds. Further, the reaction mixture was analyzed by gas chromatography to determine the amount of the products. The results obtained are shown in Table 3. In Table 3, "1,6-HD" stands for 1,6-hexanediol, and "K" is a pseudo first-order reaction rate constant given with a unit of 1/hr which was determined at a reaction period of 1 hour based on the amount of hydrogen consumed.

TABLE 3

| | | Amount | Reaction Conditions | | | Reaction Results | | | |
|---|---|---|---|---|---|---|---|---|---|
| Exa- | Catalyst | of | | Pres- | | Conver- | | | Rate |
| mple | | Amount | Water | Temp. | sure | Time | sion | Yield (mol %) | | Con- |
| No. | Kind | (g) | (g) | (° C.) | (MPa) | (hr) | Rate (%) | $C_5$—OH | $C_6$—OH | 1,6-HD stant |
| 1 | A | 4 | 80 | 220 | 10 | 4 | 98 | 1.7 | 0.5 | 83.4 |
| 2 | A | 4 | 30 | 230 | 8.5 | 4 | 98.5 | 0.4 | 0.7 | 96.2 |
| 3 | A | 4 | 30 | 230 | 15 | 3 | 99.7 | 2.0 | 0.8 | 96.3 |

TABLE 3-continued

| Example No. | Catalyst Kind | Catalyst Amount (g) | Amount of Water (g) | Temp. (° C.) | Pressure (MPa) | Time (hr) | Conversion Rate (%) | Yield (mol %) $C_5$—OH | Yield (mol %) $C_6$—OH | Yield (mol %) 1,6-HD | Rate Constant |
|---|---|---|---|---|---|---|---|---|---|---|---|
| 4 | B | 4 | 80 | 220 | 10 | 4 | 95 | 0 | 0.4 | 79.4 | |
| 5 | D | 4 | 80 | 220 | 10 | 4 | 99 | 10.3 | 0.6 | 79.2 | |
| 6 | E | 4 | 80 | 220 | 10 | 4 | 99 | 0 | 0.5 | 90.3 | |
| 7 | J | 4 | 80 | 220 | 10 | 4 | 95.9 | — | — | 79.6 | K = 0.37 |
| 8 | L | 4 | 80 | 220 | 10 | 4 | 87.9 | — | — | 57.6 | K = 0.31 |
| 9 | A | 2 | 30 | 230 | 8.5 | 4 | 96.1 | — | — | 73.1 | K = 0.32 |
| 10 | C | 4 | 80 | 220 | 10 | 4 | 95 | 0.1 | 0.4 | 79.6 | |
| 11 | F | 2 | 30 | 230 | 8.5 | 4 | 92.0 | — | — | 65.4 | K = 0.24 |
| 12 | G | 2 | 30 | 230 | 8.5 | 4 | 94.2 | — | — | 68.2 | K = 0.27 |
| 13 | M | 2 | 30 | 230 | 8.5 | 4 | 80.1 | — | — | 22.9 | K = 0.21 |
| 14 | I | 2 | 30 | 230 | 8.5 | 4 | 93.9 | — | — | 60.6 | K = 0.37 |
| 15 | K | 4 | 80 | 220 | 10 | 4 | 77.2 | — | — | 34.0 | K = 0.23 |

EXAMPLES 16 TO 19

In a 200 ml autoclave with induction stirring device were charged 80 g of water, 2 g of the catalyst shown in Table 4 below, and the starting compound(s) shown in Table 4 in an argon atmosphere. Hydrogen was introduced to a pressure of 1 MPa, and the autoclave was heated to 240° C. Hydrogen was further introduced to 10 MPa, and the hydrogenation was allowed to proceed at that temperature under that pressure for 6 hours. The reaction results are shown in Table 4.

TABLE 4

| Example No. | Catalyst | Starting Compound | Conversion Rate (%) | Yield (mol %) $C_5$-OH | Yield (mol %) $C_6$-OH | Yield (mol %) 1,6-HD |
|---|---|---|---|---|---|---|
| 16 | D | ε-caprolactone (20 g) | 96.3 | 16.1 | 2.0 | 72.4 |
| 17 | D | adipic acid (20 g) | 98.6 | 11.1 | 1.8 | 81.4 |
| 18 | D | adipic acid (8.5 g) + ε-caprolactone (11.5 g) | 96.3 | 11.3 | 1.3 | 76.9 |
| 19 | M | adipic acid (8.5 g) + ε-caprolactone (11.5 g) | 70.1 | 6.4 | 2.5 | 34 |

EXAMPLES 20 TO 22

In a 200 ml autoclave with induction stirring device were charged 20 g of the starting material shown in Table 5 below, 4 g of the catalyst A, and 30 g of water. Hydrogen was introduced to a pressure of 1 MPa, and the autoclave was heated to 230° C. Then hydrogen was introduced to a prescribed pressure, and the hydrogenation was allowed to proceed at that temperature under that pressure for a prescribed time. The reaction results are shown in Table 5. The connversion rate was calculated from the carboxyl group content of the starting material and that of the reaction mixture as measured by titration.

TABLE 5

| Example No. | Starting Material | Pressure (MPa) | Time (hr) | Conversion Rate (%) | Yield of 1,6-HD (mol %) |
|---|---|---|---|---|---|
| 20 | A | 8.5 | 4 | 96.7 | 100 |
| 21 | B | 8.5 | 4 | 97.6 | 93.9 |
| 22 | B | 15 | 3 | 98.9 | 100 |

EXAMPLES 23 TO 27

In a 200 ml autoclave with induction stirring device were charged 20 g of the starting material shown in Table 6 below, 4 g of catalyst A, 30 g of water and the additive shown in Table 6 in an argon atmosphere. Hydrogen was introduced to a pressure of 1 MPa, and the autoclave was heated to 230° C. Hydrogen was further introduced to 8.5 MPa, and the hydrogenation was allowed to proceed at that temperature under that pressure for 3 hours. The reaction mixture was allowed to stand to let the catalyst settle. The supernatant liquid was taken out, and 20 g of the starting material, 30 g of water and the additive were put in the autoclave containing the catalyst, and hydrogenation was carried out in the same manner as described above. Likewise, hydrogenation reaction was performed 6 times in total. The reaction results are shown in Table 6.

TABLE 6

| Example No. | Starting Material | Additive Kind | Additive Amount (mmol) | Yield of 1,6-HD (g/g-catalyst · hr) 1st Reaction | Yield of 1,6-HD (g/g-catalyst · hr) 6th Reaction |
|---|---|---|---|---|---|
| 23 | C | NaOH | 25 | 0.66 | 0.69 |
| 24 | C | NaOH | 50 | 0.51 | 0.51 |
| 25 | C | $CH_3COONa$ | 50 | 0.56 | 0.56 |
| 26 | D | — | — | 0.61 | 0.22 |
| 27 | E | — | — | 0.86 | 0.98 |

EXAMPLES 28 TO 31

In a 200 ml autoclave with induction stirring device were charged 20 g of the starting material shown in Table 7 below, 4 g of catalyst A, 30 g of water, and a prescribed amount of sodium sulfate in an argon atmosphere. Hydrogen was introduced to a pressure of 1 MPa, and the autoclave was heated to 230° C. Then hydrogen was introduced to 8.5 MPa, and the hydrogenation was allowed to proceed at that temperature under that pressure for a prescribed time. The reaction results are shown in Table 7.

TABLE 7

| Example No. | Starting Material | Amount of Sodium Sulfate (g) | Reaction Time (hr) | Reaction Results Conversion Rate (%) | Yield of 1,6-HD (mol %) |
|---|---|---|---|---|---|
| 28 | adipic acid (8.5 g) + ε-caprolactone (11.5 g) | 1.5 | 4 | 98.4 | 98.5 |
| 29 | adipic acid (8.5 g) + ε-caprolactone (11.5 g) | 0 | 4 | 97.7 | 92.3 |
| 30 | F | 1.5 | 3 | 97.2 | 88.5 |
| 31 | F | 0 | 3 | 96.2 | 85.2 |

EXAMPLES 32 TO 33

In a 200 ml autoclave with induction stirring device were charged 8.5 g of adipic acid, 11.5 g of ε-caprolactone, 30 g of water, a prescribed amount of sodium sulfate, and 4 g of catalyst A in an argon atmosphere. Hydrogen was introduced to a pressure of 1 MPa, and the autoclave was heated to 230° C. Hydrogen was further introduced to 8.5 MPa, and the hydrogenation was allowed to proceed at that temperature under that pressure for 3 hours. The reaction mixture was allowed to stand to let the catalyst settle, and the supernatant liquid was taken out. Into the autoclave containing the catalyst were put 8.5 g of adipic acid, 11.5 g of ε-caprolactone, 30 g of water, and a prescribed amount of sodium sulfate, and hydrogenation was carried out in the same manner as described above. The reaction results are shown in Table 8.

TABLE 8

| Example No. | Amount of Sodium Sulfate (g) | First Reaction Results Conversion Rate (%) | Yield of 1,6-HD (mol %) | Second Reaction Results Conversion Rate (%) | Yield of 1,6-HD (mol %) |
|---|---|---|---|---|---|
| 32 | 0.07 | 97.8 | 96.8 | 94.7 | 94.7 |
| 33 | 0 | 97.8 | 90 | 93.2 | 84.2 |

While the invention has been described in detail and with reference to specific examples thereof, it will be apparent to one skilled in the art that various changes and modifications can be made therein without departing from the spirit and scope thereof.

What is claimed is:

1. A process for preparing 1,6-hexanediol comprising hydrogenating a starting material containing at least one compound selected from the group consisting of adipic acid, ε-hydroxycaproic acid, ε-caprolactone and oligomers of ε-caprolactone in a liquid phase in the presence of a catalyst containing ruthenium and tin.

2. The process according to claim 1, wherein said starting material is a substance recovered from a reaction mixture resulting from liquid phase oxidization of cyclohexane for the production of cyclohexanol and cyclohexanone.

3. The process according to claim 1, wherein said starting material is a substance recovered from an aqueous solution containing alkali salts of said compounds which is obtained by extraction from a reaction mixture resulting from liquid phase oxidization of cyclohexane for the production of cyclohexanol and cyclohexanone with an aqueous alkali solution.

4. The process according to claim 1, wherein 0.1 to 80 mol % of said compound has a form of an alkali salt.

5. The process according to claim 1, wherein 5 to 50 mol % of said compound has a form of an alkali salt.

6. The process according to claim 1, wherein said liquid phase contains 1000 ppm or more of sodium sulfate.

7. The process according to claim 1, wherein said catalyst comprises activated carbon having supported thereon ruthenium and tin.

8. The process according to claim 1, wherein said catalyst comprises activated carbon having supported thereon ruthenium, tin and platinum.

9. The process according to claim 1, wherein said catalyst is prepared by supporting ruthenium and tin on activated carbon which has been treated with a nitric acid aqueous solution and dried to a water content of 7% by weight or less.

10. The process according to claim 1, wherein said catalyst is prepared by supporting ruthenium and tin on a carrier followed by reduction with hydrogen at a gas hourly space velocity of 10000 hr$^{-1}$ or less and a temperature of 260° C. or higher.

11. The process according to claim 1, wherein said catalyst is prepared by supporting ruthenium, tin, and platinum on a carrier followed by reduction with hydrogen at a gas hourly space velocity of 500 to 7500 hr$^{-1}$ and a temperature of 300 to 550° C.

12. A process for preparing 1,6-hexanediol comprising feeding (A) a starting material recovered from a reaction mixture resulting from liquid phase oxidization of cyclohexane for the production of cyclohexanol and cyclohexanone, (B) an alkali salt of a carboxylic acid selected from the group consisting of adipic acid and ε-hydroxycaproic acid, and (C) hydrogen to a reaction zone having a solid catalyst containing ruthenium and tin and carrying out hydrogenation in an aqueous medium containing sodium sulfate in a concentration of 1000 ppm or higher at a temperature of 100 to 260° C. under a pressure of 1 to 25 MPa, said starting material (A) being prepared by extracting carboxylic acids dissolved in said reaction mixture with an aqueous alkali solution, neutralizing the resulting extract containing an alkali salt of carboxylic acids with a mineral acid, extracting the carboxylic acids contained in the solution with an organic solvent to obtain an extract containing the carboxylic acids, evaporating the organic solvent of the extract to remove the organic solvent, and concentrating the residue to increase the total content of adipic acid, ε-hydroxycaproic acid, ε-caprolactone and oligomers of ε-caprolactone to 45 to 80% by weight, the concentrations of the ε-caprolactone and its oligomers being calculated as converted to ε-hydroxycaproic acid.

13. The process according to claim 12, wherein said solid catalyst is prepared by supporting ruthenium and tin on activated carbon which has been treated with a nitric acid aqueous solution and dried to a water content of 7% by weight or less and reducing the activated carbon having supported thereon ruthenium and tin with hydrogen at a gas hourly space velocity of 500 to 7500 hr$^{-1}$ and a temperature of 300 to 550° C.

14. The process according to claim 12, wherein said alkali salt of a carboxylic acid (B) is present in an amount of 0.1 to 80 mol % based on the total amount of said alkali salt (B) and the adipic acid, ε-hydroxycaproic acid, ε-caprolactone, and oligomers of ε-caprolactone contained in said starting material (A), the mole number of ε-caprolactone and oligomers thereof being calculated as converted to ε-hydroxycaproic acid.

* * * * *